United States Patent [19]
Saeki et al.

[11] Patent Number: 4,827,062
[45] Date of Patent: May 2, 1989

[54] COMPOSITION CONTAINING UBIDECARENONE WITH ABSORPTION PROMOTED

[75] Inventors: Yasuharu Saeki; Takeshi Watanabe, both of Gifu; Takayuki Ohwaki, Aichi; Masahiro Kawahara, Gifu; Yasuo Miyake, Aichi, all of Japan

[73] Assignee: Eisai Co., Ltd., Tokyo, Japan

[21] Appl. No.: 844,025

[22] Filed: Mar. 25, 1986

[30] Foreign Application Priority Data

Mar. 28, 1985 [JP] Japan ................................. 60-61927

[51] Int. Cl.$^4$ .............................................. A61K 31/12
[52] U.S. Cl. .................................... 514/690; 514/975
[58] Field of Search ............................. 514/690, 975

[56] References Cited

U.S. PATENT DOCUMENTS

| | | | |
|---|---|---|---|
| 3,198,704 | 8/1965 | Roy ..................................... | 514/975 |
| 4,572,832 | 2/1986 | Kigasawa et al. ................... | 514/774 |
| 4,617,187 | 10/1986 | Okuyama et al. .................... | 514/689 |

FOREIGN PATENT DOCUMENTS

| | | | |
|---|---|---|---|
| 118132 | 9/1984 | European Pat. Off. ............ | 514/690 |
| 55-81813 | 6/1980 | Japan ................................. | 514/690 |
| 59-148718 | 8/1984 | Japan ................................. | 514/690 |

OTHER PUBLICATIONS

McCutcheon's—Detergents & Emulsifiers—1971 Annual, pp. 125 & 159.
Chem. Abst. 94:90365r, (1981)—Tokai Capsule Co., Ltd.
Chem. Abst. 102:32098d, (1985)—Yamaguchi et al.
Chem. Abst. 104:56448k, (1986)—Mizushima et al.
Chem. Abst. 105:178330g, (1986)—Kimura et al.

*Primary Examiner*—Douglas W. Robinson
*Attorney, Agent, or Firm*—Wenderoth, Lind & Ponack

[57] ABSTRACT

A composition containing ubidecarenone, a glycerol mono-fatty acid ester and/or a propylene glycol mono-fatty acid ester, and a liquid oil. Oral administration of the composition provides a promoted absorption of ubidecarenone which is used for improving a coronary function.

7 Claims, 1 Drawing Sheet

COMPOSITION CONTAINING UBIDECARENONE WITH ABSORPTION PROMOTED

BACKGROUND OF THE INVENTION

1. Field of the Invention

The present invention relates to a composition containing ubidecarenone whose absorption is promoted.

2. Description of the Invention

Ubidecarenone is broadly utilized clinically as a medicine effective in improving the coronary function. However, it is commonly well known that ubidecarenone is poor in absorption after oral administration because it is difficult to solubilize in water. For the purpose of improving the solubility of ubidecarenone, various inventions have been proposed and include Japanese Patent Application Laid-open Nos. 18914/81; 12309/81; 148718/84; 148735/84 and 161433/82, for example. However, it is still required to further improve the solubility of ubidecarenone.

SUMMARY OF THE INVENTION

The present inventors have made various studies and have consequently discovered that a composition comprising ubidecarenone, a monoester of glycerol and a fatty acid (hereinafter referred to as "a glycerol mono-fatty acid ester") and/or a monoester of propylene glycol and a fatty acid (hereinafter referred to as "a propylene glycol mono-fatty acid ester"), and a liquid oil brings about an excellent promotion in absorption. The present invention has been thus accomplished. It is therefore an object of the present invention to provide a composition containing ubidecarenone wherein the absorption of ubidecarenone is promoted in oral administration.

According to the present invention, the above object is achieved by providing a composition which comprises, as requisite components, ubidecarenone, a glycerol mono-fatty acid ester and/or a propylene glycol mono-fatty acid ester, and a liquid oil.

BRIEF DESCRIPTION OF THE DRAWINGS

The above and other objects, features and advantages of the present invention will become apparent from the following detailed description of the preferred embodiments taken in conjunction with the accompanying drawings in which.

DETAILED DESCRIPTION OF THE PREFERRED EMBODIMENT

Figure 1:
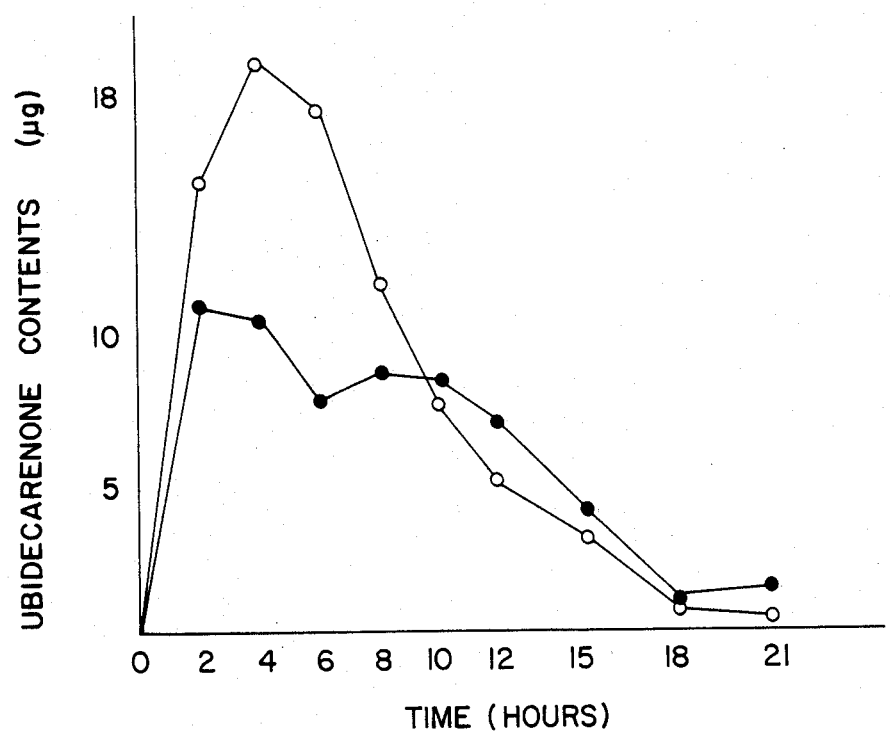
FIG. 1 is a graph illustrating a variation in ubidecarenone contents appearing in the lymph with the passage of time.

In a composition according to the present invention, a glycerol mono-fatty acid ester and/or a propylene glycol mono-fatty acid ester are/is requisite component(s).

Such a glycerol mono-fatty acid ester includes those available, specifically such as MGO (under the trade name and from Nikko Chemicals, Co. in Japan), and glycerol mono-oleic acid ester is most preferred.

As the other component, a propylene glycol mono-fatty acid ester includes those available, specifically such as PMO (under the trade name and from Nikko Chemicals, Co. in Japan), and propylene glycol mono-oleic acid ester is most preferred.

It is to be understood that the glycerol mono-fatty acid ester and the propylene glycol mono-fatty acid ester are usually employed alone, respectively, but may be, of course, employed in combination with each other. The employment of them in combination is included in the scope of the present invention.

A liquid oil is also another requisite component in a composition according to the present invention. The liquid oils includes vegetable and synthetic oils. Illustrative of such preferred vegetable oils are cotton seed oil, peanut oil, sesame oil, and olive oil. Illustrative of such preferred synthetic oils are synthetic esters of glycerol and fatty acids and diesters of propylene glycol and fatty acids such as caproic, caprylic, capric and lauric acids, or ODO and the like.

A glycerol mono-fatty acid ester and/or a propylene glycol mono-fatty acid ester and a liquid oil may be combined with ubidecarenone in any proportions. Particularly desirable effect is obtained, when the glycerol mono-fatty acid ester and/or the propylene glycol mono-fatty acid ester are/is used in an amount of 0.1 to 25 parts by weight, preferably 0.2 to 2.5 parts by weight, while the liquid oil is used in an amount of 1 to 30 parts by weight, per 1 part by weight of ubidecarenone.

Other additives may be optionally selected and added into the composition according to the present invention, and include stabilizers for a suspension such as silicic anhydride, aluminum stearate, magnesium stearate, etc., excipients for shaping the composition and the like, but it is to be understood that the present invention is not limited by such additives.

The composition according to the present invention is basically in the form of a solution or suspension in an oil. However, the composition according to the present invention may be used in the form of a powder obtained by adsorbing such an oily liquid in another powder and forming the resulting material into a powder, or a granule, tablet, syrup or sugar-coated pill, hard capsule and the like which are produced from the further treatment of such a powder. In addition, a capsule resulting from the direct encapsulation of the above oily liquid is a suitable form for the composition of the present invention. Accordingly, the composition of the present invention means those in the basic form of a liquid in an oil and a series of pharmaceutical compositions in the forms produced from such liquid in an oil.

The composition of the present invention may be prepared in a normal manner depending on the intended pharmaceutical form. For example, a composition in the form of a liquid in an oil may be prepared by blending a glycerol mono-fatty acid ester and/or a propylene glycol mono-fatty acid ester with a liquid oil, and then adding ubidecarenone thereto and vigorously stirring them in an emulsifier to form an oily liquid. A composition in the form of a powder may be prepared by covering the thus-obtained oily liquid to form a suitable powder. A composition in another form may be prepared by properly treating the above oily liquid used as a starting material.

The present invention will be more particularly described by way of examples given below, but it should be noted that the invention is not limited to those examples.

EXAMPLE 1

Five grams of ubidecarenone was added to the mixture of 10 g of glycerol/oleic monoester and 15 g of propylene glycol/caprylic diester, and the resulting mixture was vigorously stirred using an emulsifier under an ice-cooled condition to provide a suspension.

EXAMPLE 2

Five grams of ubidecarenone was added to the mixture of 4 g of glycerol/oleic monoester and 15 g of propylene glycol/caprylic diester, and the resulting mixture was vigorously stirred using an emulsifier to provide a suspension.

EXAMPLE 3

Five grams of ubidecarenone was added to the mixture of 7 g of glycerol/oleic monoester and 15 g of propylene glycol/caprylic diester, and the resulting mixture was vigorously stirred using an emulsifier under an ice-cooled condition to provide a suspension.

EXAMPLE 4

Five grams of ubidecarenone was added to the mixture of 3 g of glycerol/oleic monoester and 17 g of peanut oil, and the resulting mixture was vigorously stirred using an emulsifier to provide a suspension.

EXAMPLE 5

Five grams of ubidecarenone and 0.3 g of silicic anhydride were added to the mixture of 1 g of glycerol/oleic monoester and 21 g of propylene glycol/caprylic diester, and the resulting mixture was vigorously stirred using an emulsifier under an ice-cooled condition to provide a suspension.

EXAMPLE 6

Five grams of ubidecarenone was added to the mixture of 7 g of propylene glycol/oleic monoester and 15 g of caprylic acid/propylene glycol diester, and the resulting mixture was vigorously stirred using an emulsifier under an ice-cooled condition to provide a suspension.

EXAMPLE 7

Five grams of ubidecarenone and 1 g of silicic anhydride were added to the mixture of 4 g of propylene glycol/oleic monoester and 11 g of caprylic acid/propylene glycol diester, and the resulting mixture was vigorously stirred using an emulsifier to provide a suspension.

EXAMPLE 8

Five grams of ubidecarenone was added to the mixture of 15 g of propylene glycol/oleic monoester and 5 g of sesame oil, and the resulting mixture was vigorously stirred using an emulsifier to provide a suspension.

EXAMPLE 9

Five grams of ubidecarenone was added to the mixture of 0.5 g of glycerol/oleic monoester and 30 g of ODO, and the resulting mixture was vigorously stirred using an emulsifier to provide a suspension.

EXAMPLE 10

One gram of ubidecarenone was added to the mixture of 25 g of propylene glycol/oleic monoester and 5 g of caprylic acid/propylene glycol diester, and the resulting mixture was vigorously stirred using an emulsifier to provide a suspension.

EXAMPLE 11

One gram of ubidecarenone was added to the mixture of 2 g of glycerol/oleic monoester and 30 g of cotton seed oil, and the resulting mixture was vigorously stirred using an emulsifier under an ice-cooled condition to provide a suspension.

EXAMPLE 12

265 grams of ubidecarenone and 132.5 g of silicic anhydride were added to the mixture of 371 g of glycerol/oleic mono-ester and 795 g of caprylic acid/propylene glycol diester, and the resulting mixture was vigorously stirred using an emulsifier to provide a suspension. This suspension was encapsulated using a soft encapsulator to give an elliptic soft capsule having a content weight of 270 mg and a gross weight of 560 mg.

EXAMPLE 13

Example 1 was repeated to provide a suspension, except that 10 g of glycerol/oleic monoester were replaced by 5 g of glycerol/oleic monoester and 5 g of propylene glycol/oleic monoester.

Description will be made of the effect of the present invention in Experimental examples.

EXPERIMENTAL EXAMPLES

Samples

The suspensions prepared in the above EXAMPLES 1 to 7 were used as subject samples 1 to 7, respectively. In addition, a solution obtained by dissolving 1 g of ubidecarenone in 19 g of propylene glycol/caprylic diester was provided as a control sample A, and a suspension prepared by suspending 1 g of ubidecarenone in 4 g of glycerol/oleic monoester was provided as a control sample B.

PROCEDURE

Male SD-type rats fasted for 16 hours were subjected to a lymph collecting operation by an improved technique of Bollman method (J.L. Bollman et. al., J.Lab. Clin. Med., 33 1349 (1966)).

After the operation, the rats were allowed to freely eat a feed, and the lymph flooding conditions of them were observed for 2 days. Only the rats having a good lymph flooding condition were used. Each sample in an amount corresponding to a ubidecarenone content of 1 mg was encapsulated into a small-sized capsule for animals and administered using an oral sound, following which 1 ml of water was immediately supplied to the rats. The rats were allowed to be fasted for 12 hours after the administration.

For each sample, 7 to 10 rats were used.

The lymph was collected for every two hours up to the lapse of 12 hours and then for every three hours, and the ubidecarenone content in the lymph was determined by means of a high speed liquid chromatography (Abe, et. al., Vitamins 53 385 (1979)).

RESULTS

Figure 2:
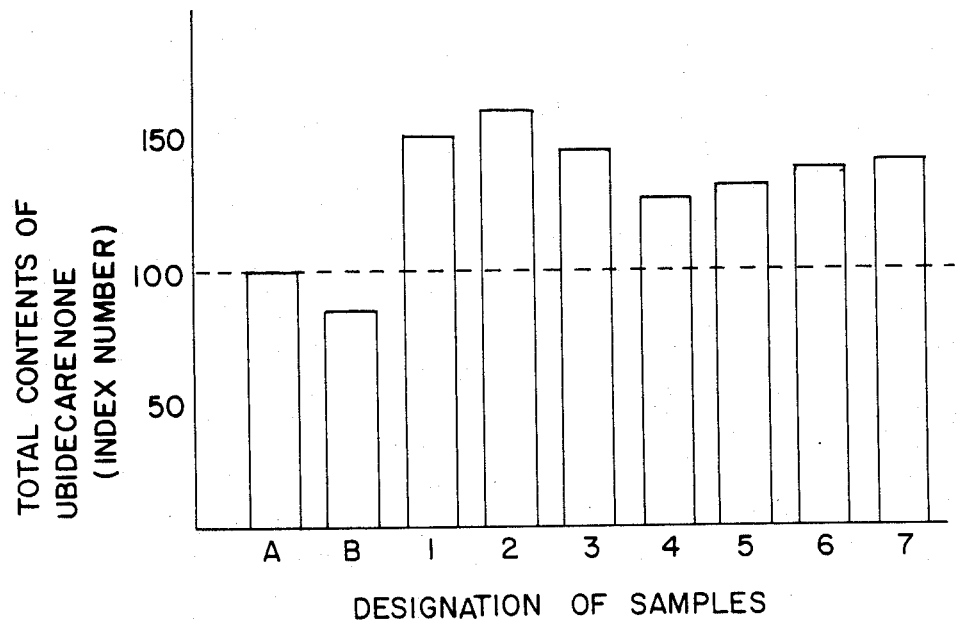
FIG. 2 is a graph illustrating the total contents appearing in the lymph for every sample in the tests.

The results are given in FIGS. 1 and 2.

FIG. 1 is a graph illustrating the variation in the ubidecarenone contents appearing in the lymph of the rats with the passage of time when the subject sample 1 or control sample A was administered. In FIG. 1, the mark O designates the result for the subject sample 1, and the mark ● denotes the result for the control sample A.

FIG. 2 is a graph illustrating the total contents of ubidecarenone appearing in the lymph of the rats up to the lapse of 10 hours after the administration when the control samples A and B and the subject samples 1 to 7 were administered, respectively.

It is to be noted that in FIG. 2, the contents of ubidecarenone is given as index numbers based on a total amount of 100 for the control sample A. In addition, the characters A and B and the numerals 1, 2—in FIG. 2 designate each sample, respectively.

It becomes apparent from FIGS. 1 and 2 that the composition of the present invention results in considerable promotion of absorption of ubidecarenone in oral administration.

What is claimed is:

1. A non-aqueous composition comprising:
   (1) ubidecarenone,
   (2) a glycerol mono-unsaturated fatty acid ester, a propylene glycol mono-unsaturated fatty acid ester, or a mixture thereof, and
   (3) a pharmaceutically acceptable liquid oil, wherein the fatty acid ester component (2) amounts to 0.1 to 25 parts by weight, and the liquid oil amounts to 1 to 30 parts by weight, per 1 part by weight of the ubidecarenone.

2. A composition as claimed in claim 1, wherein the fatty acid is oleic acid.

3. A composition as claimed in claim 1, wherein the liquid oil is a vegetable oil selected from the group consisting of cotton seed oil, peanut oil, sesame oil and olive oil.

4. A composition as claimed in claim 1, wherein the liquid oil is a pharmaceutically acceptable synthetic oil selected from the group consisting of a glycerol ester of a saturated fatty acid and a propylene glycol diester of a saturated fatty acid.

5. A composition as claimed in claim 4, wherein the synthetic oil is a propylene glycol di-saturated fatty acid ester.

6. A composition as claimed in claim 1, wherein the composition is in the form of a solution or suspension of components (1) and (2) in the liquid oil.

7. A composition as claimed in claim 1, wherein the composition is in the form of a powder, a tablet, a syrup, a hard capsule or a granule.

* * * * *